United States Patent
Ortmaier et al.

(10) Patent No.: US 8,548,779 B2
(45) Date of Patent: Oct. 1, 2013

(54) METHOD FOR DETERMINING A POSITION FOR AND POSITIONING A DETECTION DEVICE OF A NAVIGATION SYSTEM

(75) Inventors: Tobias Ortmaier, Hemmingen (DE); Dirk Jacob, Augsburg (DE)

(73) Assignee: KUKA Laboratories GmbH, Augsburg (DE)

( * ) Notice: Subject to any disclaimer, the term of this patent is extended or adjusted under 35 U.S.C. 154(b) by 794 days.

(21) Appl. No.: 12/740,031

(22) PCT Filed: Nov. 18, 2008

(86) PCT No.: PCT/EP2008/065756
§ 371 (c)(1),
(2), (4) Date: Apr. 27, 2010

(87) PCT Pub. No.: WO2009/065830
PCT Pub. Date: May 28, 2009

(65) Prior Publication Data
US 2010/0256960 A1   Oct. 7, 2010

(30) Foreign Application Priority Data
Nov. 19, 2007 (DE) .......................... 10 2007 055 205

(51) Int. Cl.
*G06G 7/48* (2006.01)
*G06F 17/50* (2006.01)
(52) U.S. Cl.
CPC .................................. *G06F 17/5018* (2013.01)
USPC ................................................... 703/7; 703/6
(58) Field of Classification Search
USPC ........................................ 703/6–7; 700/245
See application file for complete search history.

(56) References Cited

U.S. PATENT DOCUMENTS 6,366,799 B1    4/2002   Acker et al.
(Continued)

FOREIGN PATENT DOCUMENTS

EP    1 340 470 A1    9/2003
WO    2007069170 A2   6/2007

OTHER PUBLICATIONS

Hayashibe et al. "Robotic surgery setup simulation with the integration of inverse-kinematics computation and medical imaging"., Computer Methods and Programs in Biomedicine 83., 2006., p. 63-72.*

(Continued)

*Primary Examiner* — Eunhee Kim
(74) *Attorney, Agent, or Firm* — Wood, Herron & Evan, LLP

(57) ABSTRACT

The invention relates to a method for determining a position for and positioning a detection device (E) of a navigation system. First, a computer simulation of a system is done that comprises a robot (R) which has first markers (M1) of a navigation system or first prominent points, a three-dimensional object (P) which has second markers (M2) of the navigation system or second prominent points, and a detection device (E) of the navigation system. Various positions of the robot (R), the object (P), and/or the detection device (E) are simulated, and the quality of the detectability of the first markers (M1) or the first prominent points on the robot (R) and/or the second markers (M2) or the second prominent points on the object (P) are automatically determined for the simulated positions by means of the detection device (E). The determined qualities and the corresponding simulated positions and/or the simulated position having the highest or at least a sufficiently high determined quality is/are output.

18 Claims, 4 Drawing Sheets

(56) References Cited

U.S. PATENT DOCUMENTS

Figure 1:
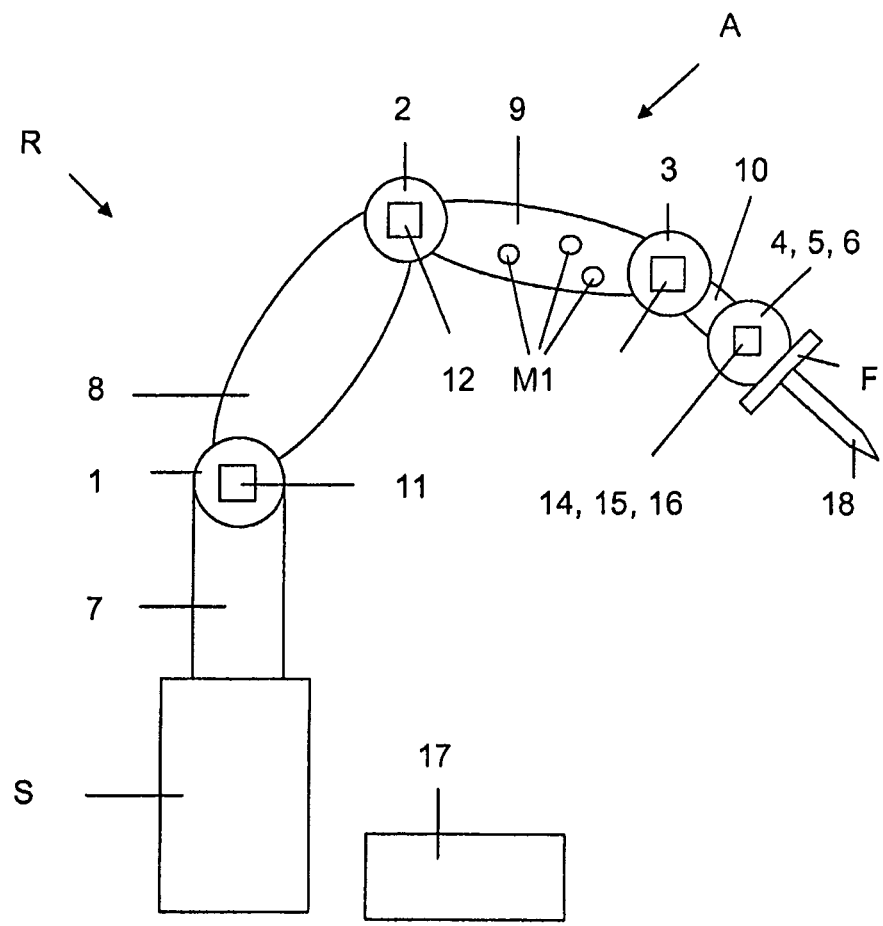

| | | |
|---|---|---|
| 6,895,268 B1 | 5/2005 | Rahn et al. |
| 6,932,506 B2 * | 8/2005 | Mitschke et al. ............. 378/207 |
| 7,447,615 B2 * | 11/2008 | Watanabe et al. ................. 703/7 |
| 2004/0015053 A1 | 1/2004 | Bieger et al. |
| 2004/0077939 A1 | 4/2004 | Graumann |
| 2004/0116803 A1 | 6/2004 | Jascob et al. |

OTHER PUBLICATIONS

European Patent Office; International Search Report in International Patent Application No. PCT/EP2008/065758 dated Jul. 24, 2009; 8 pages.

European Patent Office; International Search Report in International Patent Application No. PCT/EP2008/065756 dated Mar. 19, 2009; 4 pages.

\* cited by examiner

METHOD FOR DETERMINING A POSITION FOR AND POSITIONING A DETECTION DEVICE OF A NAVIGATION SYSTEM

The invention relates to a method for determining a position for a detection device of a navigation system and a method for positioning a detection device of a navigation system.

US 2004/0015053 A1 discloses a medical workplace with a laparoscope, a robot guiding the laparoscope, and other surgical instruments. Positioned on the laparoscope and on the surgical instruments are position sensors, which detect an electro-magnetic field, transmitted by an emitter of a navigation system. On the basis of the detected electromagnetic field, the positions of the laparoscope and of the surgical instruments in the space can be determined.

US 2004/0077939 A1 discloses a medical workplace with an X-ray apparatus, a surgical instrument, a position detection system and a robot guiding the surgical instrument for treating a patient in an at least partially automated manner. In order to detect the positions of the surgical instrument, the X-ray apparatus and the patient, position markers are arranged on the X-ray apparatus, on the patient, and on the surgical instrument or on the robot, which are registered by an optical position detection apparatus of the position detection system. Based on an evaluation of the images of the position markers recorded with the optical position detection apparatus, it is possible to determine the position, i.e., the location and orientation of the position markers, and thus of the surgical instrument, of the X-ray apparatus and of the patient in the space.

In order to be able to determine the corresponding positions, it is necessary that the position detection apparatus of the position detection system, which is also referred to as a navigation system, be able to detect the position markers sufficiently well. If the navigation system is an optical navigation system, whose position detection apparatus is realized for example as cameras, then the quality of the position determination may suffer for example if the position markers are even just partially concealed relative to the cameras.

The object of the invention is therefore to specify a method for determining a location of a detection apparatus of a navigation system, with the help of which locations for the detection apparatus relative to a robot and/or a three-dimensional object can be found, so that the position of the robot and/or of the object can be determined relatively precisely by means of the detection apparatus.

An additional object of the invention is to specify a method for positioning a detection apparatus of a navigation system relative to a robot and/or an object, so that the position of the robot and/or of the three-dimensional object can be determined relatively precisely by means of the detection apparatus.

The first problem of the invention is solved by a method for determining a position of a detection apparatus of a navigation system, having the following procedural steps:

Creating a computer simulation of a system that has
  a detection apparatus of a navigation system,
  a robot provided with first markers of the navigation system, or a robot provided with first distinctive sites, and
  a three-dimensional object provided with second markers of the navigation system, or an object provided with second distinctive sites,
simulation of various positions of the robot, the object and/or the detection apparatus by means of the computer simulation,
automatic determination of the quality of detectability of the first markers or first distinctive sites of the robot and/or of the second markers or second distinctive sites of the object by means of the detection apparatus for the simulated positions, and,
outputting of the ascertained qualities and the corresponding simulated positions and/or of the simulated position with the highest quality, or at least with sufficiently high determined quality.

It is thereby possible to adjust the positions of the robot, the object and/or the detection apparatus automatically or interactively, so that a sufficiently good quality is attained.

Navigation systems are generally known in medical technology, in particular in minimally invasive medical technology, for example from U.S. Pat. No. 6,895,268 B1. Navigation systems include the detection apparatus, which is for example an optical detection apparatus, which may for example have cameras, a laser tracking system, projectors for structured light or linear projectors. The detection apparatus is set up so as to detect in a generally known manner the second markers positioned on the object, in particular on the surface of the object, or the second distinctive sites of the object, and the first markers positioned on the robot or the first distinctive sites of the robot. On the basis of the markers or distinctive sites detected with the detection apparatus, a computing device of the navigation system is able to determine in an essentially generally known manner the positions and possibly the orientations of the object and the robot.

In order to plan in particular the positions of the object relative to the detection apparatus and/or of the robot relative to the detection apparatus, according to the invention first the computer simulation for the system consisting of robot with first markers or first distinctive sites, object with second markers or second distinctive sites, and detection apparatus of the navigation system is created.

A picture data record may be created for example for the computer simulation, in particular a three-dimensional picture data record of the object, which is for example a living being. The picture data record depicts the object, possibly a living being, and the second markers or the second distinctive sites of the object.

The detection apparatus is likewise modeled for the computer simulation, so that positions of the detection apparatus relative to the object may be simulated by means of the simulation. On the basis of this simulation, the position and possibly the orientation of the second markers or of the second distinctive sites relative to the detection apparatus can be determined, whereby the quality of the detectability of the second markers or of the second distinctive sites is determinable by means of the detection apparatus. Based on various simulated positions of the detection apparatus relative to the object, the quality of the various simulated positions can thus be calculated. It is then possible to output for example the position of the detection apparatus relative to the object, for example by means of a display apparatus, which produces the best quality of the detection, or to adjust the location of the detection apparatus automatically.

If the object is the living being, then the picture data record of the living being can be produced by means of a medical imaging apparatus. Examples of suitable medical imaging apparatuses are magnetic resonance devices, computer tomography devices, X-ray devices, in particular C-arm X-ray devices, or ultrasound devices.

The robot having the first markers or having the first distinctive sites can likewise be modeled for the computer simulation, so that here too the detectability of the first markers or first distinctive sites positioned on the robot can be simulated for various positions of the robot relative to the detection apparatus, and favorable positions can be determined thereby. In particular, the intervention and parts thereof and thus the movement of the first markers or of the first distinctive sites can be simulated. The movement of the first markers or first distinctive sites can then be used to calculate the position.

If the object is the living being, who is to lie for example on a patient-transport trolley, then the patient-transport trolley can also be modeled for the computer simulation, in order to detect for example whether the patient-transport trolley conceals the first or second markers or first or second distinctive sites with respect to the detection apparatus for a particular position, or whether the living being lying on the patient-transport trolley conceals the markers or distinctive sites depending on the orientation of the patient-transport trolley, which is for example height-adjustable.

If it is intended that the robot be moved, then the movement of the robot can be taken into account for the computer simulation. In particular, the kinematics of the movement can be taken into account for the computer simulation.

Robots in general are manipulating machines, which are equipped with useful tools for automatic handling of objects, and are programmable in a plurality of motion axes, in particular with regard to orientation, position and process sequence. Robots generally include a robot arm, which is also referred to as a manipulator, a control apparatus and possibly an effector, which may be designed for example as a gripper for gripping a tool, for example when used in medical technology, to apply a medical instrument, in particular a surgical instrument. The robot arm represents essentially the movable part of the robot, which is also referred to as the kinematics. The robot arm has in particular a plurality of axes, which are driven for example by means of electric drives, by the control apparatus in the form of a computer.

If the robot is used in the medical environment, then one embodiment of the method according to the invention provides that the robot moves a medical instrument automatically or under remote control, for example by a surgeon, in order to treat the object in the form of a living being therewith. One example of a medical instrument is an endoscope, with which the living being is to be treated.

Thus it is possible, according to one variant of the method according to the invention, to simulate a movement of the robot within the computer simulation on the basis of a desired movement of the medical instrument for treating the living being.

In particular if the method according to the invention is used in the medical environment, it is possible to offer suggestions for favorable positions of the detection apparatus of the navigation system relative to the robot and/or to the living being to a live operator during pre-operative planning for an operation on the object in the form of a living being. The movement of the robot also, in particular a planned trajection of the tip of the robot, can also be included in the consideration by means of the method according to the invention. If the operator chooses the positions independently, then on the basis of the method according to the invention a display can be obtained of the expected detectability, in particular the visibility and quality of the markers or distinctive sites, possibly enabling the operator to adjust the planned positions interactively.

The second problem of the invention is solved by a method for setting up a detection apparatus of a navigation system, having the following procedural steps:

Positioning a robot provided with first markers of a navigation system or with first distinctive sites, and a detection apparatus of the navigation system that is set up to determine the position of the robot in space on the basis of first markers or first distinctive sites detected with the detection apparatus, determining the current position of the robot relative to the detection apparatus on the basis of the positioned robot and the positioned detection apparatus, by means of the navigation system, automatically comparing the position of the robot relative to the detection apparatus with a previously simulated position of the robot relative to the detection apparatus, and outputting any variance between the current position of the robot relative to the detection apparatus and the simulated position of the robot relative to the detection apparatus.

The automatic comparison of the position of the robot relative to the detection apparatus may possibly take into account the current configuration of the robot.

The positions and orientations of the first markers or first distinctive sites relative to the structure of the robot are generally known. In contrast, the positions and orientations of the second markers or second distinctive sites situated on the patient relative to the patient's anatomy are normally unknown, but can be determined through an additional prior and generally known step. This step is usually referred to as "registering."

In order to determine a relatively favorable position of the detection apparatus of the navigation system relative to the robot, in which the detection apparatus can pick up the first markers or first distinctive sites of the robot relatively well to determine the position of the robot, the positioning of the robot relative to the detection apparatus is planned in advance, for example by means of the method described above for determining a position of a detection apparatus of a navigation system.

The implementation of this planning, i.e., the actual positioning of the detection apparatus relative to the robot, can however be difficult. According to the invention, the actual positioning of the robot and of the detection apparatus is therefore compared automatically with the planned or simulated positioning. To that end, the detection apparatus for example determines the actual position of the first markers or first distinctive sites, and thus the actual position and possibly the orientation of the robot. These are compared with the planned or simulated position and possibly orientation. If a variance is found, then it is output by displaying a notice of the variance found, for example by means of a display device.

On the basis of the current position found and the planned or simulated position of the robot, it is possible to ascertain an offset vector and/or rotation corresponding to the variance, which can then be output, in particular displayed. The offset vector or rotation can be displayed graphically, in particular within the simulated position, for example by means of a display device.

According to one variant of the method according to the invention, the degree of variance is determined, and the latter is displayed for example in color, for example by means of a display device. Thus the person or persons positioning the detection apparatus relative to the robot, by varying the actual positioning and by observing the corresponding variances, determine iteratively or empirically that position for the detection apparatus relative to the robot which corresponds relatively well to the simulated position for the detection apparatus. "Pointing to" the position of the robot and of the detection apparatus for example with a tracked pointer, is also conceivable.

According to one embodiment of the method according to the invention, a desired movement of the robot is taken into account for the simulated position of the robot.

According to another variant of the method according to the invention, the following additional procedural steps are performed:

Positioning a three-dimensional object provided with second markers or second distinctive sites, where the navigation system is set up to determine the position of the object in space using second markers detected with the detection apparatus.

determining the current position of the object relative to the detection apparatus on the basis of the positioned object and the positioned detection apparatus, automatically comparing the position of the robot relative to the detection apparatus with a previously simulated position of the robot relative to the detection apparatus, and outputting any variance between the current position of the object relative to the detection apparatus and the simulated position of the object relative to the detection apparatus.

The three-dimensional object is for example a living being, who is to be treated in particular by means of the robot. To this end the robot may carry a medical instrument, in particular a surgical instrument, in a manner planned in advance. To determine the position of the robot relative to the living being, to the object in general, there are also markers, i.e., the second markers, positioned on the surface of the latter. During the treatment of the living being with the robot, it is normally desirable that the detection apparatus be able to detect the first and second markers at all times, if possible, and accordingly that it be positioned in such a way that this condition is always fulfilled. On the basis of this variant of the method according to the invention, it is possible not only to orient the detection apparatus relative to the robot so that the latter's first markers can be detected relatively well by the detection apparatus, but also to position the detection apparatus relatively favorably relative to the object.

The positions and orientations of the second markers or second distinctive sites situated on the patient relative to the patient's anatomy are normally unknown, but can be determined through an additional prior and generally known step. This step is usually referred to as "registering." The intraoperative position of the second markers may possibly differ from the preoperative position, and thus from the simulation. An adjustment for the positions to be found may be performed after the registration if necessary.

Figure 2:
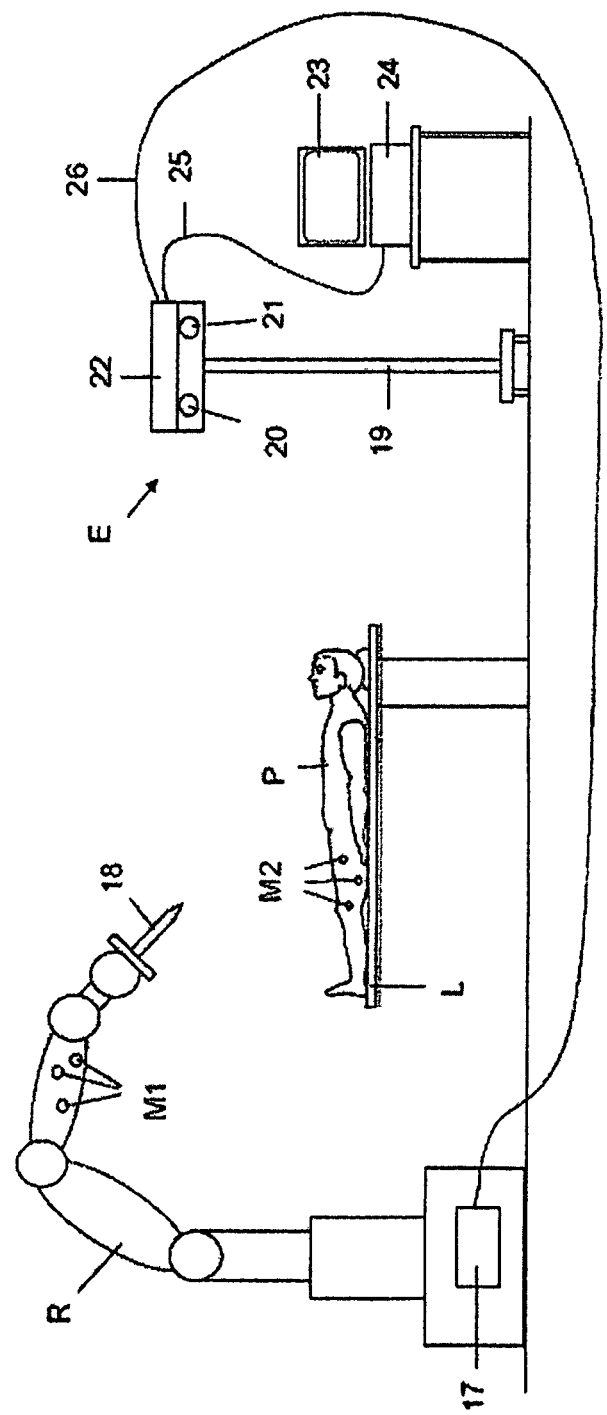
Figure 3:
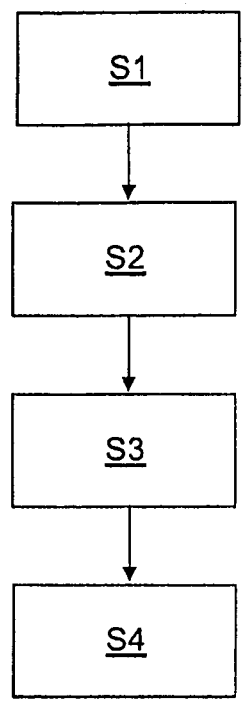
Figure 4:
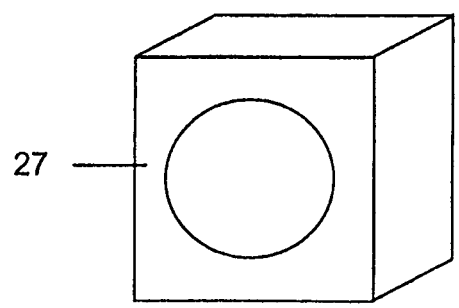
Figure 5:
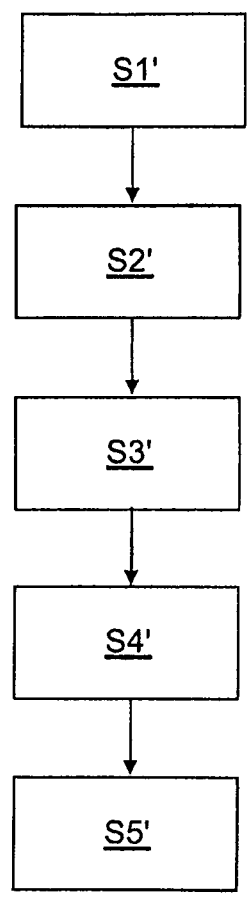

An example of an exemplary embodiment of the invention is depicted in the attached schematic drawings. The figures show the following:

FIG. 1 a robot,

FIG. 2 a medical workplace having the robot, a navigation system and a patient-transport trolley, FIG. 3 a flow chart to illustrate the determination of positions of the detection apparatus of the navigation system relative to the robot, FIG. 4 a medical imaging device, and FIG. 5 a flow chart to illustrate the positioning of the detection apparatus of the navigation system relative to the robot.

FIG. 1 shows a robot R having a robot arm A, which in the case of the present exemplary embodiment is attached to a base. Robot arm A represents essentially the movable part of robot R, and includes a plurality of axes 1-6, a plurality of levers 7-10 and a flange F, to which for example a medical instrument 18 may be attached.

In the case of the present exemplary embodiment, each of the axes 1-6 is moved with an electric drive 11-16, which drives are electrically connected in a non-depicted manner to a control computer 17 of robot R, so that control computer 17 or a computer program running on control computer 17 is able to actuate electric drives 11-16 in such a way that the position and orientation of flange F of robot R can be set essentially freely in space.

Electric drives 11-16 of robot R each include for example an electric motor and possibly power electronics that actuate the motors.

In the case of the present exemplary embodiment, robot R is intended to treat a patient P, lying in FIG. 2 on a patient-transport trolley L, with medical instrument 18. FIG. 2 also shows a navigation system that has a detection apparatus E which in the case of the present exemplary embodiment has two cameras 20, 21, markers M1 positioned on robot R, and markers M2 positioned on patient P. In the case of the present exemplary embodiment, detection apparatus E of the navigation system also includes a computer 22, and is attached to a movable stand 19 in such a way that the position of detection apparatus E in space can be changed.

Navigation systems as such are known to the person skilled in the art from sources including U.S. Pat. No. 6,895,268 B1, and are intended to determine the position and orientation of an object, for example of patient P.

Navigation systems may be for example magnetic, or as in the case of the present exemplary embodiment, optical navigation systems, and are utilized for example to determine the position and possibly the orientation of an object. In order to determine for example the position of patient P or of robot R, the navigation system determines the positions of markers M1, M2 in space by means of its cameras 20, 21.

On the basis of the positions determined for patient P and robot R, the latter can for example move medical instrument 18 in a desired manner so that patient P is treated therewith in a desired manner. In order for control computer 17 of robot R to receive information, computer 22 for example of the navigation system is connected to control computer 17 of robot R by means of a data line 26.

In order for the navigation system to be able to determine the positions of patient P and robot R with sufficient precision, it is necessary that cameras 20, 21 be able to detect markers M1, M2 sufficiently well. Hence it is necessary that detection apparatus E be positioned in a suitable manner relative to patient P and robot R.

In order to obtain at least a relatively favorable position for detection apparatus E relative to patient P and relative to robot R, in the case of the present exemplary embodiment the position of robot R, the location of patient P and the position of detection apparatus E are planned. The steps carried out in the case of the present exemplary embodiment for planning the aforementioned positions are summarized in a flow chart shown in FIG. 3.

In the case of the present exemplary embodiment, the positions of detection apparatus E and of robot R, as well as the location of patient P, are planned by means of a computer simulation, which is stored on a computer 24 in the form of a suitable computer program, step S1 of the flow chart of FIG. 3.

In the case of the present exemplary embodiment, a picture data record of patient P, in particular a three-dimensional one, is first made for the computer simulation by means of a medical apparatus 27 depicted in FIG. 4. The medical imaging apparatus 27 is for example a magnetic resonance device, a computer tomography device, an X-ray device, in particular a C-arm X-ray device, or an ultrasound device. For creating the picture data record, the markers M2 may already be positioned on patient P; they can accordingly also be depicted in the image assigned to the picture data record. The three-dimensional picture data record is loaded into computer 24, enabling the computer simulation to model patient P.

In the case of the present exemplary embodiment, models of robot R and of cameras 20, 21 are also stored in computer 24. The model of robot R also includes the marker M1 positioned on robot R. That makes it possible to simulate various positions of robot R and of detection apparatus E, and positions and/or orientations of patient P, by means of the computer simulation.

In order to obtain the best possible position of detection apparatus E relative to robot R and patient P, an operator, not depicted in greater detail in the figures, simulates various positions of detection apparatus E, robot R and patient P by means of the computer simulation, step S2 of the flow chart of FIG. 3.

In the case of the present exemplary embodiment, the computer simulation is designed so that it automatically determines the quality of detectability of the first and second markers M1, M2 for each of these simulated positions by means of cameras 20, 21, step S3 of the flow chart of FIG. 3. For example, the spacing of the markers M1, M2 relative to each other or the concealment of the markers M1, M2 by each other or by the surroundings can be drawn upon as a quality criterion.

The quality thus determined is then represented graphically on a display device 23 connected to computer 24. That enables the operator to determine empirically or automatically a best possible position of cameras 20, 21 in reference to patient P and robot R. Alternatively or in addition, the computer simulation may also be designed in such a way that it displays for example those simulated positions that yield the best or at least sufficiently good quality of detectability, after a plurality of locations have been simulated, step S4 of the flow chart of FIG. 3.

After desired positions of detection apparatus E and robot R, and the position of patient P, have been determined by means of the computer simulation, detection apparatus E and robot R are positioned and patient P is oriented on the patient-transport trolley L in accordance with the planning, i.e., the simulation.

FIG. 5 summarizes steps that are carried out in the case of the present exemplary embodiment, so that detection apparatus E, robot R and patient P are positioned or oriented as planned.

In the case of the present exemplary embodiment, a computer program runs on computer 24 that supports the operator, so that the latter is able to position robot R and detection apparatus E as planned in a relatively simple manner.

The operator starts by positioning robot R and detection apparatus E, step S1' of the flow chart of FIG. 5.

Detection apparatus E picks up the markers M1 of robot R, and then calculates the current position of robot R in space or the current position of robot R relative to detection apparatus E, step S2' of the flow chart of FIG. 5.

This result is conveyed to computer 24, which is connected to computer 22 of the navigation system by means of an electric line 25. Running on computer 24 is a computer program that compares the current position of robot R relative to detection apparatus E with the planned position of robot R relative to detection apparatus E, step S3' of the flow chart of FIG. 5. In the case of the present exemplary embodiment, the planned position of robot R relative to detection apparatus E is determined by means of the computer simulation described above.

On the basis of the planned position and the current position of robot R relative to detection apparatus E, the computer program running on computer 24 ascertains any variance of the two positions, step S4' of the flow chart of FIG. 5, and displays information about this variance on display device 23, step S5' of the flow chart of FIG. 5.

In the case of the present exemplary embodiment, the computer program running on computer 24 calculates an offset vector or a rotation between the planned and the current position of robot R relative to detection apparatus E, and visualizes it on display device 23. The offset vector indicates for example the direction in which detection apparatus E must be shifted, in order for it to be positioned as planned. The offset vector is inserted for example into a displayed depiction of the planned positions of robot R and detection apparatus E.

Alternatively, it is also possible to depict a quality of variance for the current positions of robot R and detection apparatus E from the planned positions graphically on display device 23, for example by means of different colors.

In the case of the present exemplary embodiment, there is also provision for the current location and/or orientation of patient P relative to robot R or relative to detection apparatus E to be compared with the location or orientation of patient P planned by means of the computer simulation.

In addition, it is also possible to take account in the computer simulation of a movement of robot R which the latter is to execute with medical instrument 18 to treat patient P, and possibly to compare that movement with the plan before the treatment is carried out.

It is also possible to take account of patient-transport trolley L for the computer simulation.

Instead of the first and second markers M1, M2, suitable distinctive sites on robot R or on patient P may also be used.

Although the exemplary embodiment describes an application in medical technology, applications of the method according to the invention are also conceivable outside of medicine, for example in measuring cells.

The invention claimed is:

1. A method for determining a position of a detection apparatus forming part of a navigation system, the method comprising:
generating a computer simulation including:
(a) a simulated version of the detection apparatus,
(b) a simulated version of a robot having a plurality of first markers or a plurality of first distinctive sites, and
(c) a simulated version of a three-dimensional object having a plurality of second markers or a plurality of second distinctive sites;
simulating, with the computer simulation, various positions of at least one of the simulated version of the robot, the simulated version of the object, or the simulated version of the detection apparatus;
automatically determining, with the simulated version of the detection apparatus and for the simulated positions, a quality characteristic indicative of detectability by the detection apparatus, of the plurality of first markers or the plurality of first distinctive sites of the robot, or of the plurality of second markers or second distinctive sites of the object; and
outputting at least one of:
(a) the determined quality characteristic and the simulated position of the detection apparatus associated therewith, or
(b) the simulated position of the detection apparatus having a predetermined level of the quality characteristic.

2. The method of claim 1, wherein the detection apparatus is an optical detection apparatus.

3. The method of claim 1, further comprising:
simulating, with the computer simulation, movement of the robot in space.

4. The method of claim 3, wherein simulating movement of the robot comprises accounting for kinematics of the robot.

5. The method of claim 1, wherein simulation of the three-dimensional object includes generation of a three-dimensional picture data record representative of the three-dimensional object, the picture data record including representation of locations of the plurality of second markers or the plurality of second distinctive sites relative to the object.

6. The method of claim 5, wherein the three-dimensional object is a living being.

7. The method of claim 6, wherein generation of the three-dimensional picture date record includes utilizing a medical imaging device.

8. The method of claim 6, wherein the robot is configured to move a medical instrument to treat the living being therewith.

9. The method of claim 8, further comprising:
simulating movement of the robot in response to a predetermined desired movement of the medical instrument for treating the living being.

10. A method for positioning a detection apparatus of a navigation system, the method comprising:
positioning a robot at a first predetermined location, the robot having a plurality of first markers or a plurality of first distinctive sites;
positioning the detection apparatus at a second predetermined location, the detection apparatus being configured to determine a position of the robot in space based on detection of the plurality of first markers or the plurality of first distinctive sites;
determining the position in space of the robot relative to the detection apparatus based on the position of the robot and the position of the detection apparatus;
automatically comparing the determined position of the robot relative to the detection apparatus with a computer-simulated position of the robot relative to the detection apparatus; and
outputting a variance between the detected position of the robot relative to the detection apparatus and the computer-simulated position of the robot relative to the detection apparatus.

11. The method of claim 10, further comprising:
determining the position in space of the robot based on detection of the plurality of first markers or the plurality of first distinctive sites by the detection apparatus.

12. The method of claim 10, wherein determining the computer-simulated position of the robot relative to the detection apparatus comprises:
generating a computer simulation including:
(a) a simulated version of the detection apparatus,
(b) a simulated version of the robot, and
(c) a simulated version of a three-dimensional object having a plurality of second markers or a plurality of second distinctive sites;
simulating, with the computer simulation, various positions of at least one of the simulated version of the robot, the simulated version of the object, or the simulated version of the detection apparatus;
automatically determining, with the simulated version of the detection apparatus and for the simulated positions, a quality characteristic indicative of detectability by the detection apparatus, of the plurality of first markers or the plurality of first distinctive sites of the robot, or the plurality of the plurality of second markers or second distinctive sites of the object; and
outputting at least one of:
(a) the determined quality characteristic and the simulated position of the detection apparatus associated therewith, or
(b) the simulated position of the detection apparatus having a predetermined level of the quality characteristic.

13. The method of claim 10, further comprising:
determining at least one of an offset vector or rotation value associated with the outputted variance between the detected position of the robot relative to the detection apparatus and the computer-simulated position of the robot relative to the detection apparatus; and
outputting the determined offset vector or rotation value.

14. The method of claim 10, further comprising:
determining a degree of the variance between the detected position of the robot relative to the detection apparatus and the simulated position of the robot relative to the detection apparatus; and
outputting a graphic indicator of the determined degree of variance.

15. The method of claim 10, further comprising:
comparing a desired movement of the robot with a computer-simulated movement thereof.

16. The method of claim 10, further comprising:
positioning a three-dimensional object at a third predetermined location, the three-dimensional object having a plurality of second markers or a plurality of second distinctive sites, wherein the detection apparatus is configured to detect a position of the object based on detection of the plurality of second markers or the plurality of second distinctive sites;
determining a position of the object relative to the detection apparatus based on the positioned object and the positioned detection apparatus;
automatically comparing the determined position of the object relative to the detection apparatus with a computer-simulated position of the object relative to the detection apparatus; and
outputting a variance between the determined position of the object relative to the detection apparatus and the computer-simulated position of the object relative to the detection apparatus.

17. The method of claim 16, further comprising:
in response to movement of the object, adjusting a position or orientation of the plurality of second markers or the plurality of second distinctive sites relative to the object.

18. The method of claim 16, wherein the object is a living being, the method further comprising:
moving a medical instrument associated with the robot to treat the living being therewith.

* * * * *

UNITED STATES PATENT AND TRADEMARK OFFICE
CERTIFICATE OF CORRECTION

PATENT NO.         : 8,548,779 B2                                     Page 1 of 1
APPLICATION NO.    : 12/740031
DATED              : October 1, 2013
INVENTOR(S)        : Tobias Ortmaier et al.

It is certified that error appears in the above-identified patent and that said Letters Patent is hereby corrected as shown below:

In the Claims:

Claim 7, Column 9,
Line 17 reads "dimensional picture date record includes" and should read -- dimensional picture data record includes --.

Claim 12, Column 10,
Lines 7-8 reads "or the plurality of the plurality of second markers or" and should read -- or the plurality of second markers or --.

Signed and Sealed this
Sixth Day of May, 2014

Michelle K. Lee
*Deputy Director of the United States Patent and Trademark Office*